United States Patent [19]

Lee

[11] 4,248,969
[45] Feb. 3, 1981

[54] REGENERATION OF A IMMOBILIZED ENZYME SYSTEM

[75] Inventor: Gene K. Lee, La Grange Park, Ill.

[73] Assignee: UOP Inc., Des Plaines, Ill.

[21] Appl. No.: 68,804

[22] Filed: Aug. 22, 1979

[51] Int. Cl.³ ............... C12M 11/14; C12M 11/08; C12M 11/06; B01J 31/40
[52] U.S. Cl. .................................. 435/176; 252/412; 435/180; 435/181
[58] Field of Search ............ 252/412, 414, 430, 428; 435/180–182, 174–177

[56] References Cited
U.S. PATENT DOCUMENTS

| | | | |
|---|---|---|---|
| 3,761,357 | 9/1973 | Epton | 435/181 |
| 3,836,433 | 9/1974 | Wirth et al. | 435/181 |
| 3,959,080 | 5/1976 | Orth et al. | 435/181 |
| 4,141,857 | 2/1979 | Levy et al. | 252/430 |

*Primary Examiner*—P. E. Konopka
*Attorney, Agent, or Firm*—James R. Hoatson, Jr.; Raymond H. Nelson; William H. Page, II

[57] ABSTRACT

A method for regenerating an immobilized enzyme system comprises treating the deactivated system with a base, removing excess base, treating the system with a bifunctional organic reagent which furnishes a pendant group, removing excess of said bifunctional reagent, and immobilizing fresh, active enzyme.

7 Claims, 1 Drawing Figure

Immobilized Enzyme System

Immobilized Enzyme System
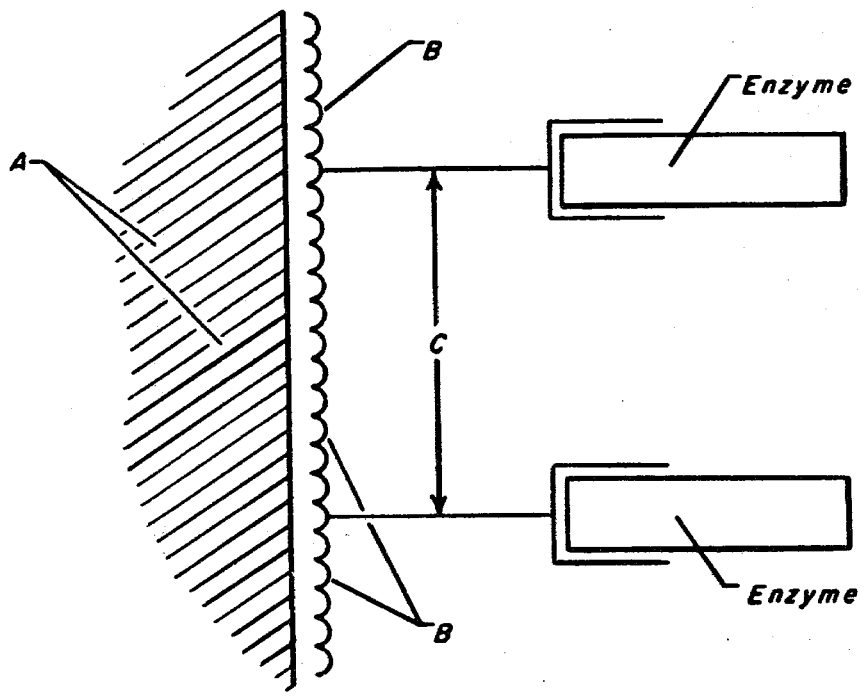

REGENERATION OF A IMMOBILIZED ENZYME SYSTEM

BACKGROUND OF THE INVENTION

Enzyme-catalyzed reactions often have the advantages of proceeding with great chemical specificity under relatively mild conditions, and often accomplish what man finds difficult, if not impossible, to duplicate in the laboratory. For such reasons there is increasing emphasis on the use of enzymatic processes on a commercial scale. One example, of many which could be cited, is the conversion of glucose to fructose using glucose isomerase.

Enzymes are water soluble, and if they are merely used in aqueous solutions recovery of enzyme for reuse is difficult and expensive. Using the enzyme only once affords a process which is relatively expensive. Consequently, many techniques have been developed for immobilizing the enzyme in such a way that substantial enzymatic activity is displayed while the enzyme itself remains rigidly attached to some water-insoluble support, thereby permitting reuse of the enzyme over substantial periods of time and for substantial amounts of feedstock. One illustration of a method for immobilizing an enzyme is found in Levy and Fusee, U.S. Pat. No. 4,141,857, where a polyamine is adsorbed on a metal oxide such as alumina, treated with an excess of a bifunctional reagent, such as glutaraldehyde, so as to cross-link the amine, thereby entrapping the resulting polymer in the pores of the metal oxide, and then contacting the mass with enzyme to form covalent bonds between the pendant aldehyde groups and an amino group on the enzyme.

The useful life of an immobilized enzyme system is limited by a continual decrease in enzymatic activity. Among the many mechanisms which lead to enzyme deactivation in such systems are: poisoning of the enzymes by impurities in the feedstock; other chemical modification of the enzyme; denaturation of the enzyme; rupture of the bond between the pendant group and the enzyme leading to dissolution of the enzyme; cleavage of the bond between the pendant group and the intermediate binding layer; loss of the binding layer as, for example, by physical ablation or cleavage of the chemical bond which hold it to the support.

Whatever the mechanism of the enzyme deactivation, reactivation of a deactivated immobilized enzyme system would prove to be a substantial advance in the art as well as being economically highly desirable. At least conceptually, two distinct approaches to reactivation are possible. One mode would be to rejuvenate the enzyme itself, i.e., assuming no physical loss of enzyme the transformations which rendered it inactive would be reversed and the enzyme would revert to its initial active state. The alternative is to restore the immobilized enzyme system to that state initially present immediately prior to attachement of enzyme, so that it would be capable of binding fresh, active enzyme once again. This invention relates to the latter approach.

SUMMARY OF THE INVENTION

An object of this invention is to regenerate an immobilized enzyme system which has become substantially deactivated. An embodiment of this invention resides in a process for regenerating an immobilized enzyme system comprising treating the system with a base as an enzyme stripping agent, removing the base, treating the system with a bifunctional organic molecule which serves as a pendant group, and removing the excess of bifunctional organic molecule, so as to put the system in a state where fresh, active enzyme can be immobilized by suitable means. A more specific embodiment of this invention resides in the application of this process to a system wherein the binding layer is an organic polymeric material and the pendant functional moiety can bond covalently with an enzyme without greatly destroying its activity. Another more specific embodiment of this invention is the application of this process wherein the enzyme is glucose isomerase and the stripping agent is an alkali metal hydroxide, such as sodium hydroxide and potassium hydroxide. Other objects and embodiments will be apparent from the description provided herein.

It is to be emphasized again that enzymes are merely representative of one class of reactive chemical entities which may be immobilized to act in some chemical process. Therefore, this invention encompasses regeneration of any immobilized reactive chemical entity which has become substantially deactivated.

DESCRIPTION OF THE FIGURE

Many immobilized enzyme systems, such as that described above, have a common conceptual basis which is depicted pictorially in the FIGURE. It is to be understood that enzymes are merely one class of reactive chemical entities which may be immobilized and subsequently utilized in a chemical process.

There is a central core support, A, whose primary purpose is to provide mechanical and thermal stability to the system and which is chemically inert in the enzymatic reaction. The intermediate primary layer, B, provides an interface between the core and the pendant groups, C. This layer may be held to the core either by physical entrapment, as within the pores of A, by strong short-range physical and/or chemical forces, as by surface adsorption or absorption, or by chemical binding to the surface of the core support. The pendant groups, C, may be part of the molecular structure of the binding layer, or may be chemically bonded to a suitable site on the binding layer. Such pendant groups are characterized by the presence of a chemically reactive functionality, usually terminally situated, which can covalently bond to some part of the enzyme, or other reactive chemical entity, sufficiently removed from its "active site" so as not to interfere substantially with its catalytic activity.

DESCRIPTION OF THE INVENTION

Although several kinds of immobilized enzyme systems are available, those wherein the enzyme is covalently bonded to a support seem to offer the best compromise between enzyme availability to feedstock and long-term immobility on a supporting structure. Accordingly, emphasis is placed on stripping deactivated enzyme and regenerating an active immobilized enzyme in such a system. This invention relates to the structure depicted in the Figure. The central core support, A in the figure, may be a metal oxide, preferably alumina and silica, glass, a ceramic or a metal. It needs to provide structural integrity, especially mechanical strength, have good characteristics in a system where there is a liquid flow, and provide a surface, wholly or in part, to which a layer of organic material can be attached either by physical or chemical means, or by a combination of the latter.

The binding layer, B, may be an organic polymer or a resin. Examples of such binding layers include functionalized polyethylenes, polyamines cross-linked with agents such as dialdehydes and diisocyanates, and others known to those skilled in the art. In a preferred embodiment, the binding layer is a polyamine such as polyethyleneimine, tetraethylenepentamine, ethylenediamine, diethylenetriamine, triethylenetetramine, pentaethylenehexamine, hexamethylenediamine, phenylenediamine, and the like, cross-linked via a reagent selected from the group consisting of dialdehydes and the diisocyanates, as for example glutaraldehyde, succindialdehyde, toluenediisocyanate, and the like. In another preferred embodiment the binding layer is a functionalized polystyrene, such as aminopolystyrene, cross-linked by one of the aforementioned reagents.

The pendant group, C, may be an independently functionalized group of the polymer, as for example an aldehydic moiety attached via mediating carbon atoms to a polyethylene chain, an independently functionalized group of a resin, or an unreacted terminus of the cross-linking agent wherein the other terminus is covalently bonded to the binding layer. In a preferred embodiment, the pendant group arises from a cross-linking agent selected from the group consisting of dialdehydes and diisocyanates.

In some instances the demarcation between core support, A, binding layer B, and pendant group C may seem indistinct. For example, the binding layer may appear to be part of the core, and might even contain a functional group which can covalently bond to an enzyme, thereby providing an immobilized enzyme system. A representative of this class is a chemically modified glass whose surface bears an organic residue having a functional group capable of covalently bonding to an enzyme. This invention relates to such a system, and to all systems which are functionally equivalent to, or can be functionally described by, the representation in the figure, however that may be attained in any particular immobilized enzyme system. The combination of structures A, B and C forms a support system; addition of enzyme forms an immobilized enzyme system.

The method of stripping and regeneration taught herein may be applied to any reactive molecule which can react with the pendant functional group without substantial loss of chemical activity; enzymes form an important class of such reactive molecules. Examples of such enzymes include glucose isomerase, glucose amylase, lactase, cellulase, glucose oxidase, trypsin, papain, hexokinase, chymotrypsin, acylase, invertase, protease, pepsin, rennin, xylanase, etc. It is to be understood that these enzymes are cited solely for illustrative purposes and it is not to be construed as a limitation of this invention. Other enzymes may be utilized, but not necessarily with equivalent results.

The physical form of the immobilized enzyme system generally is determined by factors extraneous to the stripping-regeneration process. Thus, the system may be in the form of pellets of, for example, 1/16 inch size, or it may be in the form of smaller spheres of, for example, 60-80 mesh. Although the form in which the immobilized enzyme system is used may necessitate different optimum parameters in the stripping-regeneration process, the basic method remains unchanged.

Immobilized enzyme systems in which the enzyme has become totally inactive, or nearly so, may be unpacked from the columns where they had been used and placed in containers. To this may be added sufficient enzyme stripping reagent such that the pellets or spheres are completely covered with liquid. Among the stripping reagents which are suitable for use are alkaline materials. Examples of such reagents include the alkali metal hydroxides and carbonates, such as those of lithium, sodium, potassium, cesium and rubidium, ammonia, ammonium carbonate, quaternary ammonium hydroxides such as tetramethylammonium hydroxide, benzyltrimethylammonium hydroxide, cetylpyridinium hydroxide, etc. The concentration of the reagent and amount used are not critical, provided that there is sufficient reagent to remove all inactive enzyme, and that the volume is sufficient to provide adequate contact with the pellets or spheres. Concentrations of base employed may range from about 0.01 to about 5 molar. The temperature at which stripping is conducted may be from about 20° C. to about 75° C., preferably from about 50° C. to about 70° C. Contact time may be from about 1 to about 30 minutes, preferably from about 1 to about 10 minutes, and may be accompanied by agitation. In one embodiment, the reagent is sodium hydroxide.

After the material has been treated with the base for an appropriate time, excess reagent may be removed by decantation. The pellets or spheres are then washed thoroughly with water to remove any base adhering to the surface. When no more base is present the system is ready for contacting with a solution which furnishes the pendant group. For example, the solution may be one of glutaraldehyde in water, where the concentration of glutaraldehyde is not material so long as there is present sufficient material to replace any pendant groups lost in its prior history. Where the pendant group is reactive toward water, the enzyme support system may have to be dried, by means which will be obvious to those skilled in the art, prior to treatment with the reagent. Although the system generally will be treated with a solution which furnishes the pendant group originally present, it may be treated with a solution which furnishes a different pendant group. Representatives of materials furnishing a pendant group enumerated solely for the purpose of illustration, include glutaraldehyde, succindialdehyde, terepthaladehyde, and toluenediisocyanate.

When the enzyme support system has been contacted with a solution furnishing the pendant groups for a time sufficient to replace all those previously lost, which time may vary from about 30 minutes to about 5 hours, depending on the nature of the support system, its history, the stripping reagent used and the nature of the pendant group, it is washed thoroughly to remove unreacted but adhering molecules which furnish the pendant group. At this stage the support system is rejuvenated, which is to say that it approximates its condition prior to initial enzyme immobilization. The support system is now ready to accept fresh, active enzyme to regenerate an immobilized enzyme system whose activity approximates that obtained with a new support. In the case, for example, of a polyethyleneimine binding layer crosslinked with excess glutaraldehyde, glucose isomerase may be immobilized by contacting the support system, with agitation, with an aqueous solution of the enzyme for 2 to 24 hours at a temperature from about 0° to about 50° C. preferably from about 0° to about 10° C. However, it is not an object of this invention to teach how enzymes are best immobilized given a particular support, thus it suffices to say that the support regenerated by the method of this invention is treated with enzyme in whatever way is appropriate for immobilization of that particular enzyme on a particular support system.

The description above is for a stripping-regeneration process run in a batchwise method. However, the process of this invention may be done in a continuous manner where such a mode is advantageous. Thus, as an example where the stripping agent is potassium carbonate and the reagent furnishing the pendant group is glutaraldehyde, the deactivated immobilized enzyme system in a column may be treated with a potassium carbonate solution recirculated or passed through the column for a time sufficient to remove all enzyme. Thereafter the column may be washed with water until all traces of alkaline material are removed, followed by treatment with recirculated glutaraldehyde solution until there is no further uptake of the latter reagent. Unreacted but adhering glutaraldehyde may be removed by treatment with fresh water, after which active enzyme may be immobilized by suitable means.

Whether the stripping portion of the process of this invention consists of selective removal of spent enzyme from the pendant group, or whether it consists of removal of the pendant group from the binding layer, or some combination thereof, is not known. This invention is meant to encompass removal of spent enzyme from an enzyme support system of the type described herein whatever the mechanism of removal.

The following examples serve merely to illustrate the process of this invention, and it is to be understood that this invention is not limited thereto.

EXAMPLE 1

An immobilized enzyme system based on polyethyleneimine (PEI) on alumina cross-linked with glutaraldehyde and bearing glucose isomerase had an initial activity of 1400 units per gram. The bed, composed of 60–80 mesh particles, was treated with 2 M NaOH in an amount of 20 ml solution of base per gram of bed material. This mixture was heated with stirring at 60° F. for 5 minutes, after which the solution was removed by decantation. The solid was then stirred with water sufficient to cover all material present and liquid was decanted. This washing procedure was repeated until the wash liquid was neutral (pH 7). At this stage the material displayed no enzymatic activity. Regeneration was accomplished by adding a 2.5% aqueous solution of glutaraldehyde in an amount equal to 18 ml. per gram of bed for about one hour. Excess glutaraldehyde was removed by thorough washing with water. A preparation of fresh, active glucose isomerase was contacted with the regenerated support system for 18 hours at 4° C. with continual shaking. The immobilized enzyme system was thoroughly washed with water to remove adhering but mobile enzyme. The resulting immobilized enzyme system had a glucose isomerase activity of 820 units per gram, or 59% of the activity originally present.

EXAMPLE 2

The immobilized enzyme system was like that of Example 1 but in 1/16" pellets. Its initial activity was 141 units per gram of bed. Deactivated bed material was treated with sodium hydroxide using the procedure given in Example 1. After reimmobilization of glucose isomerase the system showed a glucose isomerase activity of 121 units per gram, or 86% that originally present.

I claim as my invention:

1. A method for regenerating a used organic-inorganic support matrix comprising an organic polymeric material having functionalized pendant groups coupled with immobilized enzymes which method comprises:
   (a) treating said used support matrix containing immobilized enzymes with a basic stripping agent selected from the group consisting of ammonia, ammonium carbonate, quatenary ammonium hydroxides and carbonates and hydroxides of alkali metals at stripping conditions which include a temperature of from about 20° C. to about 75° C.;
   (b) washing said treated support matrix containing immobilized enzymes and said basic stripping agent to remove said basic stripping agent from said treated support matrix;
   (c) treating said washed support matrix of step (b) with a bifunctional organic molecule selected from the group consisting of glutaraldehyde, succindialdehyde terephthaladehyde and toluendediisocyanate to attach pendant organic molecules to said washed support matrix wherein said pendant organic molecules attached to said support matrix are sufficient to replace former pendant organic molecules removed through said use of said support matrix;
   (d) washing said support matrix containing said newly attached pendant organic molecules to remove excess organic molecules from said treatment of step (c); and
   (e) immobilizing fresh active enzymes by coupling said enzymes to said newly attached pendant organic molecules.

2. The method of claim 1 wherein said support matrix system is comprised of a central core to which is attached a binding layer, a pendant functional group anchored at the nonfunctional end to said binding layer, and wherein said functional group is capable of covalently bonding to said enzymes.

3. The method of claim 2 wherein said central core is selected from the group consisting of aluminum oxide, silicon oxide, glass and a ceramic material.

4. The method of claim 2 wherein said binding layer is selected from the group consisting of cross-linked polyamines and cross-linked aminopolystyrenes.

5. The method of claim 4 wherein said binding layer is a polyamine selected from the group consisting of polyethyleneimine, tetraethylenepentamine, ethylenediamine, diethylenetriamine, triethylenetetramine, pentaethylenehexamine, hexamethylenediamine, and phenylenediamine, and the cross-linking agent is selected from the group consisting of glutaraldehyde, succindialdehyde, and toluenediisocyanate.

6. The method of claim 1 wherein said basic stripping agent is selected from the group consisting of sodium hydroxide, potassium hydroxide, lithium hydroxide, sodium carbonate, potassium carbonate, lithium carbonate, ammonia, ammonium carbonate, and quaternary ammonium hydroxides.

7. The method of claim 1 wherein the enzyme immobilized is selected from the group consisting of glucose isomerase, glucoamylase, and cellulase.

* * * * *